(12) United States Patent
Kessler et al.

(10) Patent No.: US 10,230,050 B2
(45) Date of Patent: Mar. 12, 2019

(54) AMINO PHOSPHAZENE BASES AS N-DOPANTS IN ORGANIC ELECTRONICS

(71) Applicant: Siemens Aktiengesellschaft, Munich (DE)

(72) Inventors: Florian Kessler, Hoechstadt an der Aisch (DE); Stefan Regensburger, Neumarkt (DE); Günter Schmid, Hemhofen (DE)

(73) Assignee: SIEMENS AKTIENGESELLSCHAFT, Munich (DE)

( * ) Notice: Subject to any disclaimer, the term of this patent is extended or adjusted under 35 U.S.C. 154(b) by 0 days.

(21) Appl. No.: 15/544,490

(22) PCT Filed: Dec. 7, 2015

(86) PCT No.: PCT/EP2015/078749
§ 371 (c)(1),
(2) Date: Jul. 18, 2017

(87) PCT Pub. No.: WO2016/116202
PCT Pub. Date: Jul. 28, 2016

(65) Prior Publication Data
US 2018/0019396 A1  Jan. 18, 2018

(30) Foreign Application Priority Data
Jan. 19, 2015 (DE) .......... 10 2015 200 699

(51) Int. Cl.
*H01L 51/00* (2006.01)
*C07F 9/6524* (2006.01)
(Continued)

(52) U.S. Cl.
CPC ............ *H01L 51/005* (2013.01); *C07F 9/065* (2013.01); *C07F 9/572* (2013.01); *C07F 9/6506* (2013.01);
(Continued)

(58) Field of Classification Search
CPC . H01L 51/005; H01L 51/0059; H01L 51/002; H01L 51/0052; H01L 51/0072
See application file for complete search history.

(56) References Cited

U.S. PATENT DOCUMENTS

| 8,859,110 B2 | 10/2014 | Fuchs et al. ................ 428/690 |
| 2006/0279204 A1 | 12/2006 | Forrest et al. ............... 313/506 |

(Continued)

FOREIGN PATENT DOCUMENTS

| DE | 102012217587 A1 | 3/2014 | ............ C07C 13/15 |
| JP | 0512990 A | 1/1993 | ............ H01J 1/312 |

(Continued)

OTHER PUBLICATIONS

Machine Translation of JP2006278549.*
(Continued)

*Primary Examiner* — Julia Slutsker
(74) *Attorney, Agent, or Firm* — Slayden Grubert Beard PLLC

(57) ABSTRACT

The present invention relates to n-dopants for doping organic electron transport materials, wherein the n-dopants have at least one aminophosphazene group of formula 1 having 4 nitrogen atoms bonded to a phosphorus atom.

(Continued)

US 10,230,050 B2
Page 2

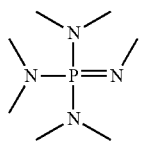

formula 1

9 Claims, 3 Drawing Sheets

(51) Int. Cl.
| | | |
|---|---|---|
| C07F 9/6593 | (2006.01) | |
| C07F 9/6584 | (2006.01) | |
| C07F 9/06 | (2006.01) | |
| C09D 5/24 | (2006.01) | |
| C07F 9/572 | (2006.01) | |
| C07F 9/6506 | (2006.01) | |
| H01L 51/50 | (2006.01) | |

(52) U.S. Cl.
CPC ........ *C07F 9/6524* (2013.01); *C07F 9/65815* (2013.01); *C07F 9/65848* (2013.01); *C09D 5/24* (2013.01); *H01L 51/002* (2013.01); *H01L 51/0052* (2013.01); *H01L 51/0072* (2013.01); *H01L 51/5076* (2013.01)

(56) References Cited

U.S. PATENT DOCUMENTS

| | | | | |
|---|---|---|---|---|
| 2007/0037010 | A1* | 2/2007 | Vestweber | ............ H01L 51/002 428/690 |
| 2011/0108772 | A1 | 5/2011 | Zeika et al. | ................... 252/500 |
| 2011/0266525 | A1 | 11/2011 | Lecloux et al. | ................ 257/40 |
| 2013/0285027 | A1 | 10/2013 | Loebl et al. | ..................... 257/40 |
| 2014/0203254 | A1 | 7/2014 | Dorok et al. | ..................... 257/40 |
| 2015/0243889 | A1 | 8/2015 | Schmid et al. | ................. 438/99 |
| 2016/0020409 | A1 | 1/2016 | Adachi et al. | ................... 544/35 |
| 2016/0293896 | A1* | 10/2016 | Rausch | ............... H01L 51/5036 |

FOREIGN PATENT DOCUMENTS

| | | | | |
|---|---|---|---|---|
| JP | 2006278549 | | * 10/2006 | |
| JP | 2007273978 | A | 10/2007 | |
| JP | 2008031348 | A * | 2/2008 | |
| JP | 2008535266 | A | 8/2008 | |
| JP | 2010062334 | A | 3/2010 | ........... H01L 21/225 |
| JP | 2013509726 | A | 3/2013 | |
| JP | 2014502041 | A | 1/2014 | |
| WO | 2016/116202 | A1 | 7/1916 | ................ C09F 9/06 |
| WO | 2014/136758 | A1 | 2/1917 | |
| WO | 2009/153276 | A1 | 12/2009 | ............ C07F 9/6581 |
| WO | 2012/175219 | A1 | 12/2012 | ................ C07F 9/06 |
| WO | 2012/175535 | A1 | 12/2012 | ............. H01L 51/05 |

OTHER PUBLICATIONS

Butour, Jean-Luc, "Spectrofluorometric and Spectrophotometric Investigations of Cyclophosphazene-DNA Complexes," Journal of Molecular Structure, vol. 65, pp. 51-60, Sep. 28, 1979.
Allcock, Harry R. et al., "Quaternized Cyclic and High Polymeric Phospazhenes and Their Interactions with Tetracynoquinodimethane," Inorganic Chemistry, vol. 25, pp. 2281-2288, Sep. 24, 1985.
Schwesinger, Von Reinhard et al., "Peralkylierte Polyaminophosphazene-Extrem Starke Neutrale Stickstoffbasen," Angew. Chem., vol. 99; No. 11, pp. 1212-1214 (German language w/ English Statement of Relevance), 1987.
Núñez, Andrés et al., "Bell-Shaped pH-Rate Profile in a Reaction Involving a Pentacoordinated Phosphorus Intermediate," Journal of Organic Chemistry, vol. 61, pp. 8386-8390, Apr. 18, 1996.
Lawson, Gavin T. et al., "Cis-Tri Hydrogen Cyclotriphosphazenates-Acidic Anions in Strongly Basic Media," Chemical Communications—Royal Society of Chemistry, vol. 5, pp. 341-342, Jan. 26, 2000.
Bickley, Jamie F. et al., "Supramolecular Variations on a Molecular Theme: The Structural Diversity of Phosphazenes $(RNH)_6P_3N_3$ in the Solid State," The International Journal for Inorganic, Organometallic and Bioinorganic Chemistry, vol. 7, pp. 1235-1244, Feb. 26, 2003.
Kaljurand, Ivari et al., "Acid-Base Equilibria in Nonpolar Media. 4. Extension of the Self-Consistent Basicity Scale in THF Medium. Gas-Phase Basicities of Phosphazenes," The Journal of Organic Chemistry, vol. 68, No. 26, pp. 9988-9993, Apr. 28, 2003.
Ishikawa, Tsutomu, "Superbases for Organic Synthesis—Guanidines, Amidines, Phosphazenes and Related Organocatalysts," Wiley, ISBN: 978-0-470-51800-7, 340 Pages, 2009.
Vorontsov, Ivan I. et al., "X-ray Crystal Structures and OFT Calculations of Differently Charged Aminocyclophosphazenes," Journal of Molecular Structure, vol. 928, No. 1-3, pp. 1-11, Mar. 12, 2009.
Kondoh, Azusa et al., "Phosphazene-Catalyzed Intramolecular Cyclization of Nitrogen-Tethered Alkynylesters," Chemical Communications—Royal Society of Chemistry, vol. 49, No. 87, pp. 10254-10256, Sep. 10, 2013.
German Office Action, Application No. 102015200699.9, 9 pages, dated Aug. 11, 2015.
Database Registry (Online) Chemical Abstracts Service, Columbus, Ohio, US, XP002755228, 1 page, Feb. 29, 2016.
Harashina, Hatsuhiko et al., "Odorless Stable Polyacetals, Their Manufacture Including Heat Treatment, Their Compositions, and Their Moldings," XP002754874, 6 pages, Feb. 29, 2016.
International Search Report and Written Opinion, Application No. PCT/EP2015/078749, 54 pages, dated Mar. 16, 2016.
Japanese Office Action, Application No. 2017537399, 9 pages, dated Oct. 16, 2018.

* cited by examiner

AMINO PHOSPHAZENE BASES AS N-DOPANTS IN ORGANIC ELECTRONICS

CROSS-REFERENCE TO RELATED APPLICATIONS

This application is a U.S. National Stage Application of International Application No. PCT/EP2015/078749 filed Dec. 7, 2015, which designates the United States of America, and claims priority to DE Application No. 10 2015 200 699.9 filed Jan. 19, 2015, the contents of which are hereby incorporated by reference in their entirety.

BACKGROUND OF THE INVENTION

For components in organic electronics it is customarily the case that the lower the voltage drop across the transport layers with p- (hole) or n- (electron) conductivity that are contained in these components, the greater the efficiency of the components. This functional relationship is valid especially for organic light-emitting diodes (schematic layer construction represented in FIG. 1) and organic solar cells (FIG. 2). For organic field-effect transistors (FIG. 3), similar relationships apply, and in these cases the efficiency of the injection of charge carriers is dependent, in particular, on the level of the contact resistances. If this can be minimized, an increase is obtained in the effective mobility of the semiconductor. Established in the art, in addition to the use of suitable electrically conducting organic materials, is the introduction into the layers of additional substances whose effect is to increase the intrinsic conductivity of these materials. Depending on the desired purpose, a distinction is made here between p- and n-dopants, which improve the p- or the n-conductivity of transport/contact layers, respectively. The number of n-dopants available for these organic-electronic components is very limited, thereby restricting the design possibilities and present technical performance of organic components. Consequently, in addition to the use of suitable dopants in OLEDs, the utilization of these dopants in field-effect transistors for contact doping, particularly in the case of complementary circuits and/or in bipolar components, is very important.

There are certain places within the literature where the synthesis and the properties of phosphazenes are addressed. One example is the book "Superbases for Organic Synthesis—Guanidines, Amidines, Phosphazenes and Related Organocatalysts" by Tsutomo Ishikawa (WILEY, 2009, ISBN: 978-0-470-51800-7). This complex of topics is also treated, for example, in Núñez et al., J. Org. Chem. 1996, 61, 8386, which includes a description of the synthesis of hexaimida-zolylcyclotriphosphazene. There is no statement made concerning the fields of use of these substances within organic electronics.

Within the patent literature, the use of specifically substituted phosphazenes in organic electronics as electron conductors is mentioned. For example, WO 2009/153276 A1 discloses an organic light-emitting diode containing at least one cyclic phosphazene compound of the following formula

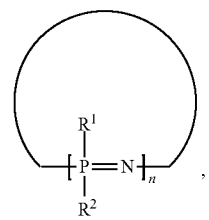

a light-emitting layer composed of at least one matrix material and at least one emitter material, the at least one matrix material comprising at least one cyclic phosphazene compound, the use of cyclic phosphazene compounds in organic light-emitting diodes, and a device selected from the group consisting of stationary screens, mobile screens, and lighting units comprising at least one organic light-emitting diode of the invention and selected cyclic phosphazene compounds, and methods for their production.

WO 2012 175219 A1 discloses an electronic device which comprises a compound A-B, where

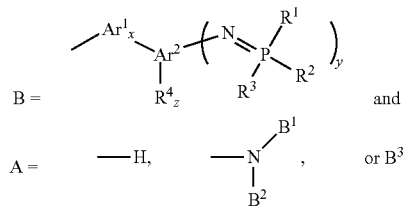

in which $-Ar^1$ is a C6-C18 arylene, which may be mono- or polycyclic and may optionally be substituted by one or more C1-C10 alkyl or C3-C10 cycloalkyl groups, $-Ar^2$ is a C6-C18 arene skeleton which is optionally substituted by electron-donating groups $R^4$, $-B^1$ and $B^2$ independently are selected from B and $Ar^2$, $-B^3$ is selected independently from the same group as B, $-R^1$, $R^2$ and $R^3$ independently are selected from alkyl, arylalkyl, cycloalkyl, aryl and dialkylamino, $-X$ is selected from 0, 1, 2 and 3, where for x>1 each Ar1 may be different, $-y$ is a nonzero integer up to the total number of valence sites, on the arene skeleton, $-z$ is an integer from zero up to the total number of valence sites on the arene skeleton minus y, and also a corresponding compound of formula AB.

The use of specifically substituted aminophosphazenes as n-dopants for increasing the conductivity of organic electron conductors, and not as electron conductors themselves, on the other hand, is not suggested by the prior art.

SUMMARY OF THE INVENTION

It is therefore an object of some embodiments of the present invention to provide a class of substances which are capable, through doping of organic electron conductors, of significantly increasing the conductivity of said conductors. It is a further object of some embodiments of the invention to provide methods by which n-transport layers are obtainable which exhibit improved conductivity, and also the provision of organic-electrical components comprising these transport layers.

According to some embodiments of the invention, methods are provided for producing n-conducting organic-electrical layers. The inventive methods may comprise depositing an n-dopant comprising at least one aminophosphazene group of the formula

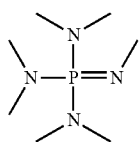

with an organic electron transport material. In a preferred embodiment, the present inventive methods provide that the n-dopants and the electron transport materials upon deposition react with one another. Preferably, according to some embodiments, a layer comprising an n-dopant volume % thickness concentration of about ≥0.01% and about ≤30% is formed.

According to other embodiments, the invention provides further methods for producing n-conducting organic-electrical layers. The methods may comprise depositing an n-dopant with an electron transport material wherein the n-dopant has the formula 2 below

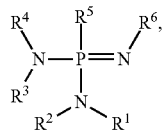

wherein $R^1$ to $R^4$ independently of one another are selected from the group of R comprising a bond, H, D, C1-C60 saturated or unsaturated alkyl, cycloalkyl, heteroalkyl, heterocycloalkyl; C1-C60 aryl, alkylaryl, heteroaryl; $R^5$ is selected from $NR_2$ and $[-N=P(NR_2)_2-]_n$ where n=1 to 5; and $R^6$ is selected from the group of R and $[-P(NR_2)_2=N-]_n$ where n=1 to 5, it being possible for the substituents independently of one another to be joined to form cyclic units. Preferably, the dopants are compounds having noncyclic aminophosphazene scaffolds. In addition, according to some embodiments, upon deposition of the n-dopants and the electron transport materials, the n-dopants and the electron transport materials may react with one another.

According to further embodiments, the present invention provides methods for producing n-conducting organic-electrical layers. The methods may comprise depositing an n-dopant comprising ≥2 and ≤7 aminophosphazene groups of the formula

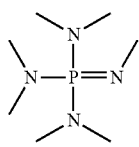

with an organic electron transport material. The n-dopant preferably comprises at least one compound of formulae 3-28:

formula 3

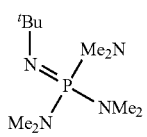

formula 4

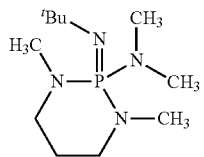

formula 5

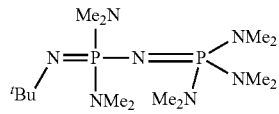

formula 6

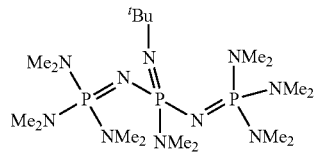

formula 7

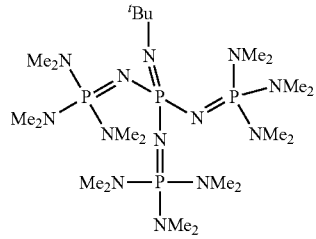

formula 8

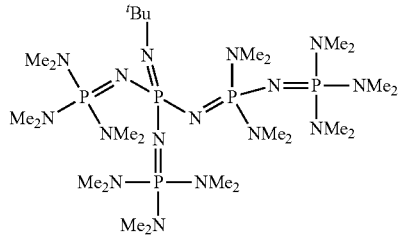

formula 9

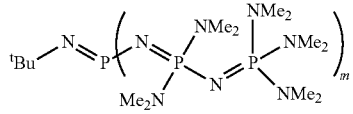

formula 10

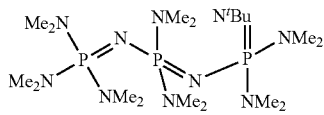

formula 11

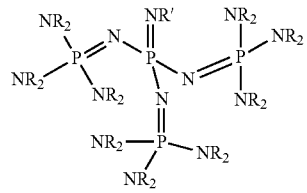

formula 12

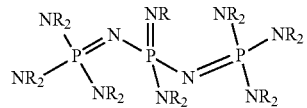

formula 13
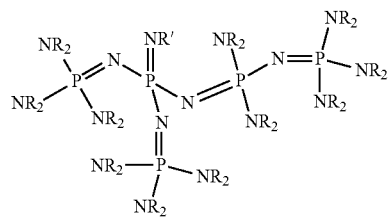
formula 14
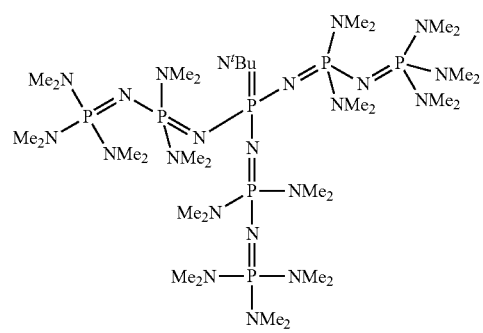
formula 15
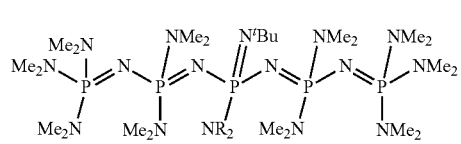
formula 16
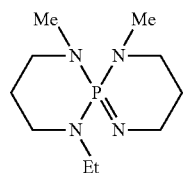
formula 17
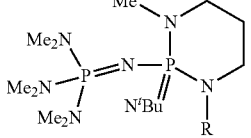
formula 18
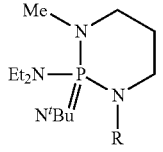
formula 19
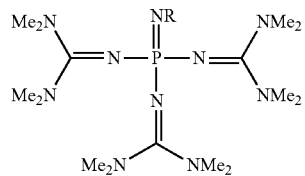
formula 20
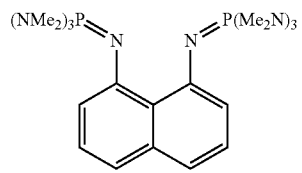
formula 21
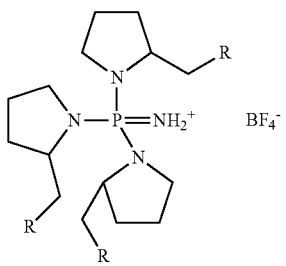
formula 22
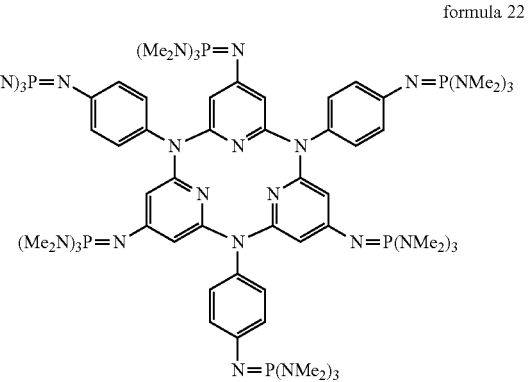
formula 23
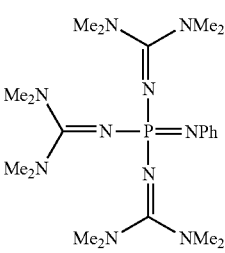
formula 24
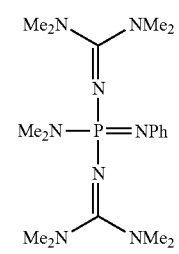
formula 25
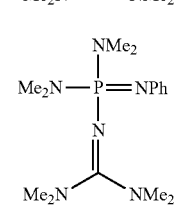
formula 26
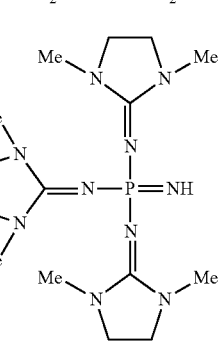

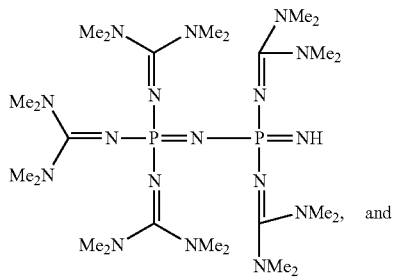

formula 27

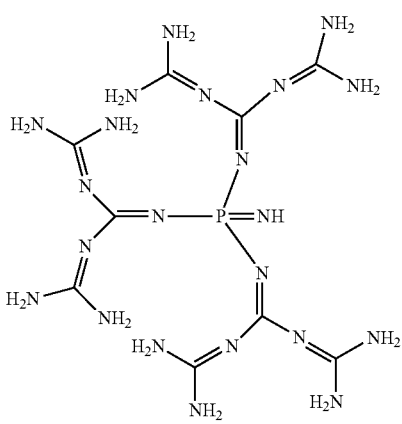

formula 28 where m in formula 9 is ≥1 and ≤5. Preferably, according to some embodiments, the methods provide for the formation of n-conducting organic-electrical layers comprising a n-dopant volume % thickness concentration of ≥0.01% and ≤30%.

BRIEF DESCRIPTION OF THE FIGURES

The properties of the n-dopants of the invention, and possible embodiments of electrical components in which the dopants may be used, are elucidated in more detail below.

DETAILED DESCRIPTION OF THE PREFERRED EMBODIMENTS OF THE INVENTION

Figure 1:
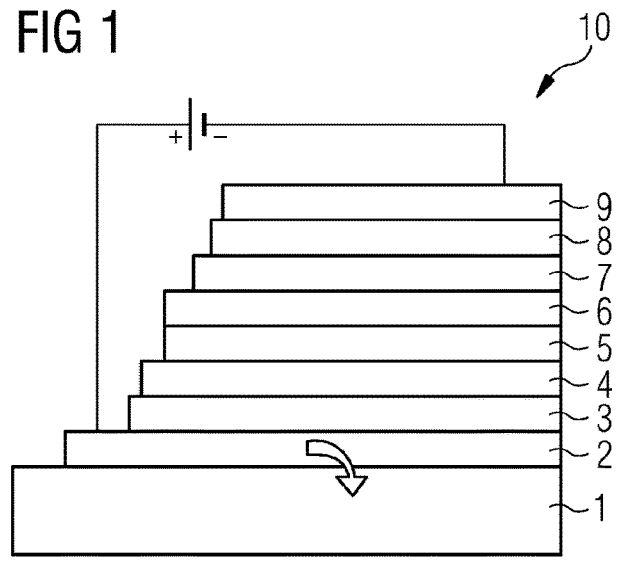
FIG. 1 shows diagrammatically the structure of an organic light-emitting diode (10). The light-emitting diode is composed of a glass layer (1); silicone or indium-tin oxide (ITO) layer (2); hole injector layer (3); hole transport layer (HTL) (4); emitter layer (EML) (5); hole blocker layer (HBL) (6); electron transport layer (ETL) (7); electron injector layer (8); and a cathode layer (9).
Figure 2:
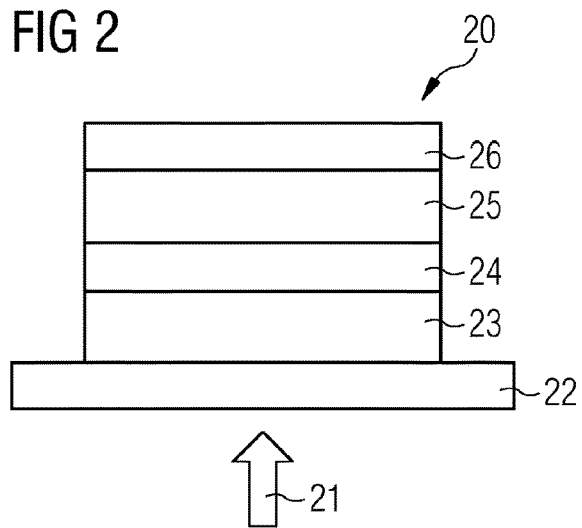
FIG. 2 shows diagrammatically the structure of an organic solar cell with PIN structure (20), which converts light (21) into electrical current. The solar cell consists of a layer of indium-tin oxide (22); a p-doped layer (23); an absorption layer (24); an n-doped layer (25); and a metal layer (26).
Figure 3:
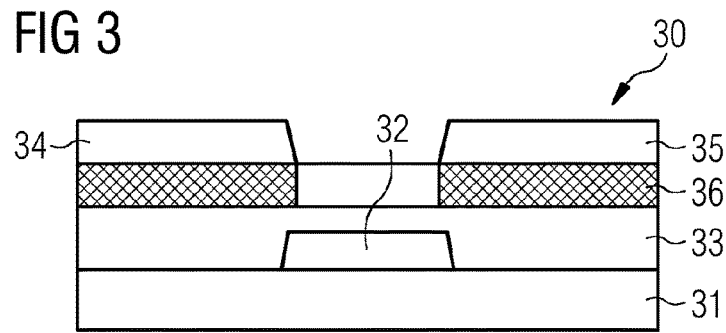
FIG. 3 shows diagrammatically a possible cross section of an organic field-effect transistor (30). Applied on a substrate (31) are a gate electrode (32), a gate dielectric (33), a source and drain contact (34+35), and an organic semiconductor (36). The shaded areas show the areas at which contact doping is useful.

In accordance with an embodiment of the invention, the n-dopant for doping organic electron transport materials is characterized in that the n-dopant has at least one aminophosphazene group of formula 1

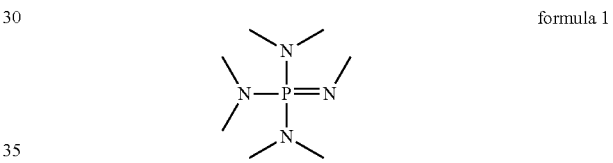

formula 1 having 4 nitrogen atoms bonded to a phosphorus atom. It has been discovered, surprisingly, that n-dopants which have an aminophosphazene group of Formula 1, in particular, are capable of significantly increasing the electron conductivity of organic electron transport materials. This effect is not attributable to the intrinsic conductivity of the n-dopants of the invention, but instead results from the interaction of the n-dopants of the invention with electron transport materials. This significant increase in conductivity can be obtained not only with substances which have only aminophosphazene groups as functional units, but also with substances in which the aminophosphazene group represents only one constituent of the functional groups in the molecule. Without being bound by a theory, it is believed that the improved suitability for increasing the electron conductivity derives from the fact that the functional aminophosphazene group is particularly electron-rich, by virtue of the 4 nitrogen atoms bonded to the phosphorus atom. This gives this aminophosphazene group an unusual basicity, which allows particularly effective interaction with organic electron transport materials and leads to a particularly effective doping outcome. This contrasts with phosphazene compounds which do not have 4 nitrogen atoms bonded to a phosphorus atom. These compounds, indeed, exhibit reduced basicity and, accordingly, are less suitable as n-dopants. Additionally, the aminophosphazenes of the invention prove, in the context of their use in organic electronics, to be very stable chemically, active kinetically, and deployable multilaterally. One possible mechanism for the increase in the conductivity is evident from the scheme below:

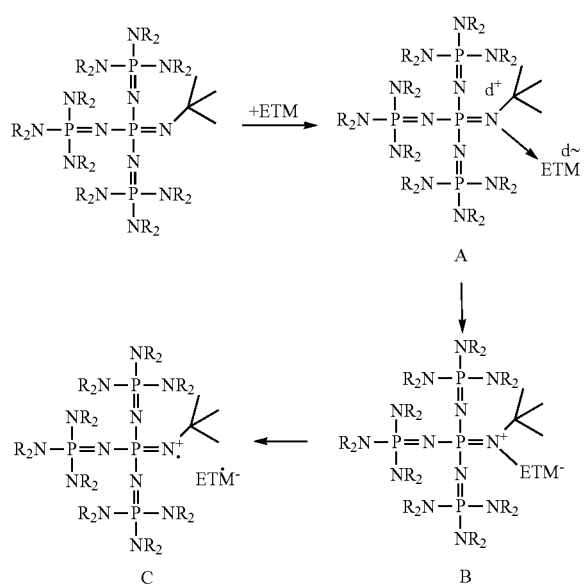

There are various conceivable doping mechanisms. On one hand, there may be association of the dopant with the electron transport material (ETM), thus forming a "charge transfer complex" (structure A). This complex has new limiting orbitals (HOMO or SOMO and LUMO), whose energetic positions enable good interaction (e.g., hopping of an electron from the "charge transfer complex" onto a matrix molecule) with undoped matrix molecules, thereby achieving increased conductivity. On the other hand, the transfer of a whole charge from the dopant to the matrix may result in an increase in its electron density and hence also in its conductivity (structure B). In this case, the ETM molecule may also dissociate again from the dopant, thereby forming a radical anion of the matrix and a radical cation of the phosphazene dopant (structure C). By virtue of the specific structure of the aminophosphazene group, a resonance-stabilized compound may be obtained, which may be the cause of the fast kinetics and effective doping.

An aminophosphazene group in the sense of the invention refers to a compound which has at least one aminophosphazene group of the formula 1 in the molecule. This may be an uncharged molecule or else a salt compound having ions, in which case at least one ion comprises an aminophosphazene group. Significant for the aminophosphazene group is the attachment of 4 nitrogen atoms to the central phosphorus atom. This central unit may be repeated in the dopant and, moreover, a plurality of aminophosphazene groups may also be joined to one another linearly or cyclically. Moreover, it is also possible, however, for the dopant of the invention to have further functional groups as well as the aminophosphazene groups.

In accordance with an embodiment of the invention, the substances having at least one aminophosphazene group are used as n-dopant. This means in particular that it is not in accordance with the invention for these substances to be used alone within a layer in an organic-electronic component. The reason is that the basic conductivity of this class of compound is inadequate for effective organic-electronic components. This dopant, then, is intended for interaction with an electron transport material. Here it has been discovered that the HOMO levels of the n-dopants of the invention are apparently such that they are able to interact effectively with the LUMO levels of the common electron transport materials. A dopant in this context, therefore, is a substance which is deposited together with the electron transport material by production methods known to the skilled person. It is especially preferred here for the molar fraction of the n-dopant in the layer not to be above the molar fraction of the electron transport material. The concentration of the n-dopants of the invention in a layer are usually much lower than that of the electron transport material. When deposited as an individual substance in a layer, moreover, the n-dopants of the invention have a much lower electrical conductivity than layers comprising electron transport materials. The joint deposition significantly increases the maximum conductivity of the electron transport materials and, moreover, there is a much higher current flow even at lower voltages. Further underpinning the n-dopant function is the fact that in p-conducting layers, the n-dopants of the invention act as blocking materials. They also do this in contradistinction to electron transport materials.

In a further embodiment, the n-dopants may conform to formula 2 below formula 2

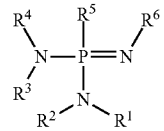

Where $R^1$ to $R^4$ independently of one another are selected from the group of R comprising a bond, H, D, C1-C60 saturated or unsaturated alkyl, cycloalkyl, heteroalkyl, heterocycloalkyl; C1-C60 aryl, alkylaryl, heteroaryl;

$R^5$ is selected from $NR_2$ and $[-N=P(NR_2)_2-]_n$ where n=1 to 5; and $R^6$ is selected from the group of R and $[-P(NR_2)_2=N-]_n$ where n=1 to 5, it being possible for the substituents independently of one another to be joined to form cyclic units. n-Dopants with the substitution pattern indicated above have proven particularly suitable for the doping of electron transport materials. Without being tied to any theory, it is believed that this may be attributable to the fact that the stated substituents significantly increase the basicity of the compound, producing improved doping in conjunction with electron transport materials. Another result of the stated substitution of the aminophosphazene group is to obtain a sterically suitable molecule which can be processed effectively in both wet and dry processes and which subsequently exhibits little tendency to crystallize in conjunction with the electron transport materials. This may mean that components containing layers of these substances may have a significantly extended life. The individual substituents bonded to the nitrogen atoms of the aminophosphazene group may in each case form ring structures with one another. Examples of these joined substituents are indicated below. It is in accordance with an embodiment of the invention, furthermore, that one or more aminophosphazene units may be associated via $[-P(NR_2)_2=N-]_n$ units to form cyclic structures. These cyclic structures, in particular, may allow charges which arise in the doping context to be distributed across the whole of the inner rings. This may contribute to particularly stable and effective doping. Further substitution of the nitrogen atoms in the formula $[-P(NR_2)_2=N-]_n$ is dependent on whether there are further functional groups following or whether the group in question is a terminal group. Examples of these compounds having a plurality of aminophosphazene units which carry a plurality of aminophosphazene groups are indicated later on below.

In an additional characteristic of the n-dopants, the substituents $R^1$-$R^4$ may independently of one another be selected from the group of R' comprising a bond, C1-C20 substituted or unsubstituted alkyl, cycloalkyl;

$R^5$ is selected from $NR'_2$ and $[-N=P(NR'_2)_2-]_n$ where n=1 to 5; and $R^6$ is selected from the group of R' and $[-P(NR'_2)_2=N-]_n$ where n=1 to 5, it being possible for the substituents independently of one another to be joined to form cyclic units. The short- to medium-chain alkyl and cycloalkyl substituents specifically lead to particularly good suitability of the n-dopants for increasing the conductivity of electron transport materials. Without being tied to a theory, it is believed that this is very likely due to the inductive effect of these substituents, which leads to increased basicity on the part of the functional group. Apparently, moreover, the steric architecture of these substituents is such that there is very rapid and effective interaction with electron transport materials.

In a further embodiment of the invention, the layer thickness concentration (volume %) of the n-dopants in a layer may be ≥0.01% and ≤30%. Within this concentration range it is possible with the n-dopants of the invention to achieve a sufficient increase in the n-conductivity of electron transport layers. Higher concentrations of n-dopants are less preferable, since the result may be a reduction in the conductivity of the layers. This can be attributed to the fact that the fraction of electron conductor in the layer becomes too small. As already mentioned above, the aminophosphazenes of the invention are particularly suitable as an n-dopants and not as electron transport materials. In a further embodiment of the invention, the molar concentration of the n-dopants in a layer may be ≥0.1% and ≤25%, preferably ≥1% and ≤20%. Quantitative determination of the molar fractions of substances within a layer is known to the skilled person. For example, the layers may be dissolved and analyzed by common quantitative determination methods, such as HPLC, for example.

In one additional aspect of the invention, furthermore, the number of aminophosphazene groups in the dopant may be ≥2 and ≤7. In view of the basicity of the aminophosphazene groups that can be used in accordance with the invention, and in view of the resultant interaction with the electron transport material, it may be an advantage for the dopants to carry a higher number of aminophosphazene groups. Without being tied to a theory, it is believed this enables the dopant to interact with a plurality of molecules of the matrix material or, possibly, to transfer a plurality of charges to the matrix material. This may contribute to increasing the conductivity of the layer. Furthermore, the interactions with a plurality of matrix molecules may result in a decrease in the crystallization tendency of the layer. This may contribute to prolonged shelf life of components comprising these layers.

In one preferred embodiment, the dopants may be a compound having a noncyclic aminophosphazene scaffold. The linear dopants which contain at least one aminophosphazene group have proven to be particularly suitable for the doping of organic electron transport materials. Without being tied to any theory, it is believed that this is very likely due to the fact that the steric properties of this class of substances permit particularly effective approximation to the electron transport materials, which may lead subsequently to very rapid and efficient charge transfer. Additionally, the linear geometry of the n-dopants may mean that because of the reduced tendency toward crystallization, organic components containing this class of substance attain a longer life.

In one particularly preferred embodiment of the invention, the dopants may comprise at least one compound of the formulae 3-28 below:

formula 3

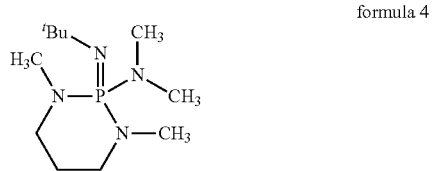

formula 4

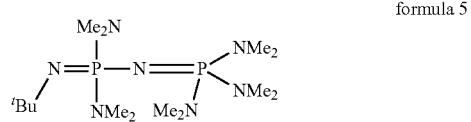

formula 5

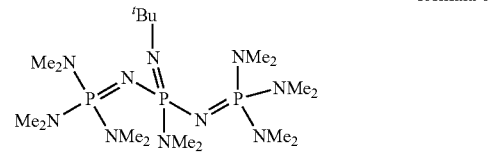

formula 6

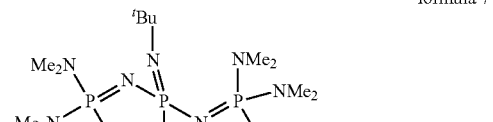

formula 7

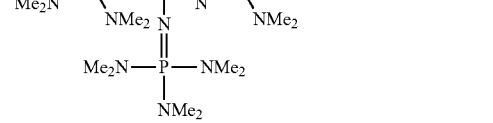

formula 8

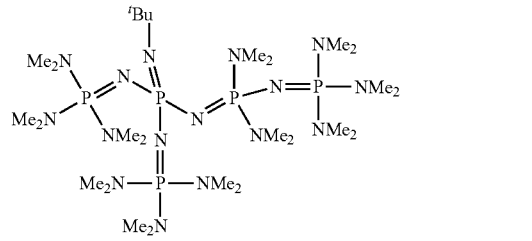

formula 9

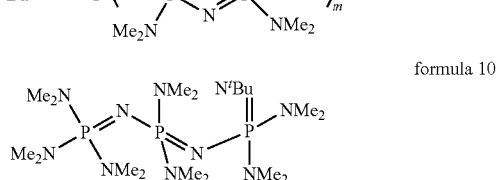

formula 10

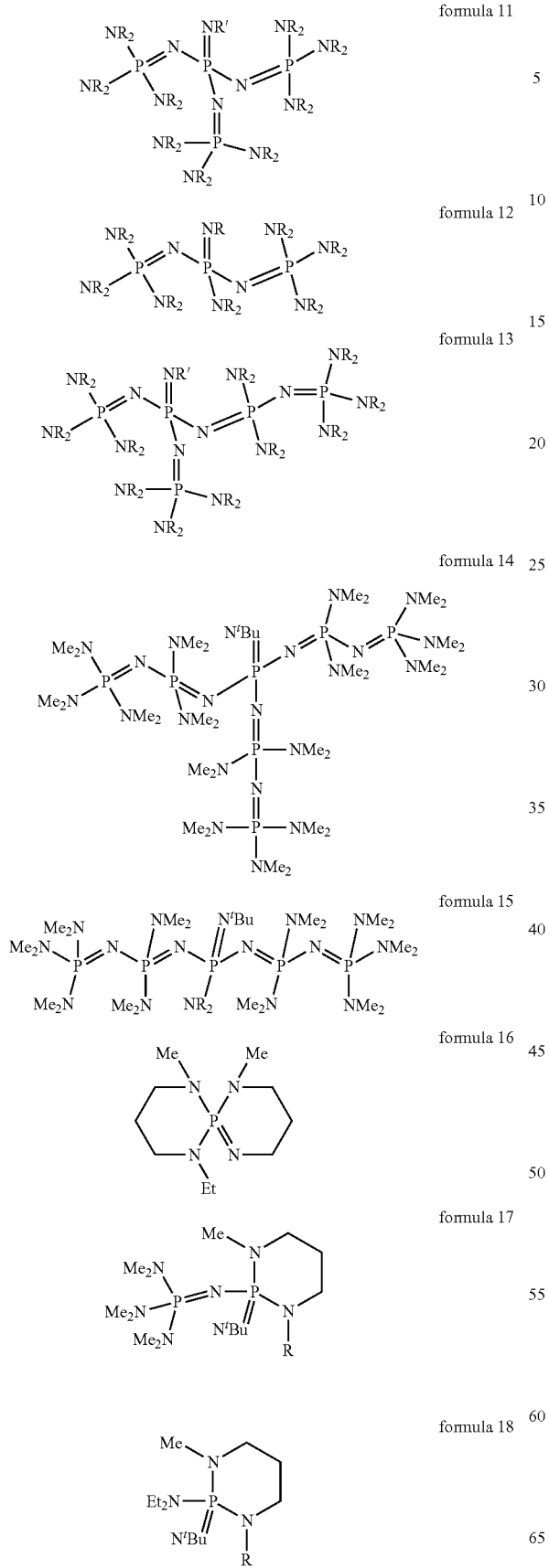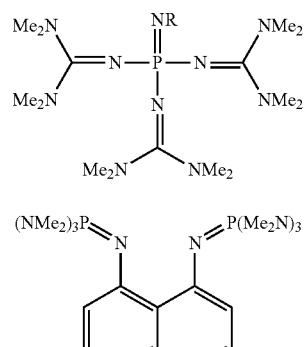

-continued

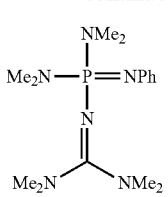
formula 25

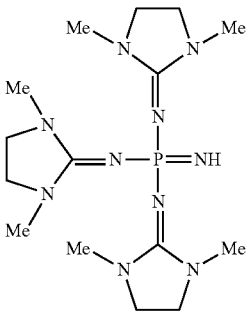
formula 26

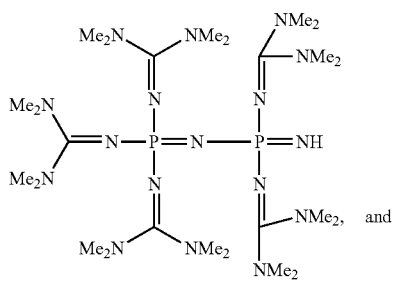
formula 27

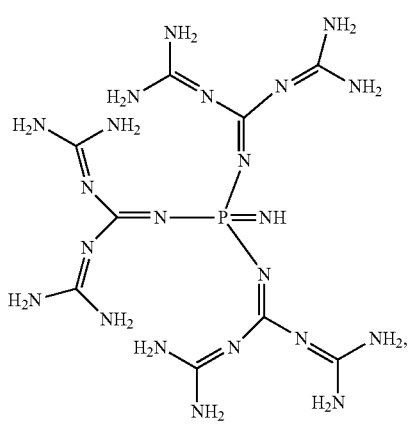
formula 28 where m in formula 9 is ≥1 and ≤5. It has been discovered that the compounds of the formulae 3-28 are especially suitable for the doping of conventional electron transport materials. The substituent pattern of these dopants in particular is in a position to provide compounds which can be processed by both wet and dry processes. The spatial properties of the substituents selected, moreover, appear to be very suitable, together with organic electron transport materials, for forming layers which are distinguished by particularly low crystallization tendency. This may lead to a longer life of organic-electronic components.

Additionally in the sense of the invention are n-dopants where ≥1 and ≤4 substituents of the $R^1$-$R^4$ and $R^6$ are tert-butyl substituents ($^t$Bu). The aminophosphazene compounds in which tertiary-butyl groups are bonded to the nitrogen atoms, in particular, are notable for a particularly good doping effect.

Without being tied to a theory, it is believed the reason for this may be that the tertiary-butyl groups have not only suitable inductive properties but also a suitable steric architecture which is capable not only of raising the basicity of the compound but also of enabling easy access of the matrix materials to the dopant. A higher number of tertiary butyl groups may be less advantageous, since in that case access of the matrix material may be hindered.

In one particular embodiment of the invention, the dopants may have a cyclic structure with two to four linked aminophosphazene units. The cyclic structures of the aminophosphazene units may be in a position to achieve particularly effective doping of electron transport materials. This may be the likely a result of the fact that the basicity of the compound is boosted further by cyclic arrangement. Furthermore, the charges which occur after doping can be distributed effectively across the whole ring system. As a function of the number of linked aminophosphazene units, accordingly, the linking of 2 units produces a 4-membered ring, the linking of 3 units produces a 6-membered ring, and the linking of 4 units produces an 8-membered ring. This ring size also permits effective processing of the compounds both in wet processes and in vacuum deposition. Larger ring structures, in contrast, may be a disadvantage, since in these cases the effective evaporation of the substances may be hindered.

In an additional aspect of the invention, at least one of the substituents on each noncyclic nitrogen may be a C1-C60 alkyl, cycloalkyl, aryl or heteroaryl radical which is bonded via a carbon, it being possible for the individual substituents to be joined to one another. It has discovered that the substitution of the noncyclic nitrogen atoms by the above-stated substitution pattern allows a particularly suitable increase in the basicity of the aminophosphazene compounds without causing any negative effect on the kinetics of a subsequent conversion reaction with electron transport materials. For this reason, therefore, it may be advantageous for at least one of the substituents on the noncyclic nitrogen atoms to be occupied by one of the substituents indicated above.

In one preferred embodiment of the invention, each of the substituents on each noncyclic nitrogen may be a C1-C30 alkyl, cycloalkyl, aryl or heteroaryl radical which is bonded via a carbon, it being possible for the individual substituents to be joined to one another. Apparently, as a result of the electronic properties of the substituents indicated above, particularly effective n-dopants may be formed, probably because of the inductive effects. In particular, the short- to medium-chain alkyl and aryl compounds appear particularly suitable for this purpose. These compounds are easily processed in both wet and vacuum processes, and yield doped layers possessing long-term stability.

In some embodiments of the invention, the dopants may comprise at least one of the following formulae 29-35 below:

formula 29
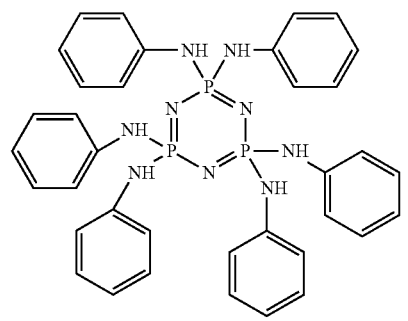

formula 30
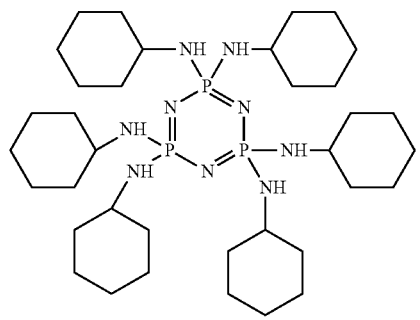

formula 31
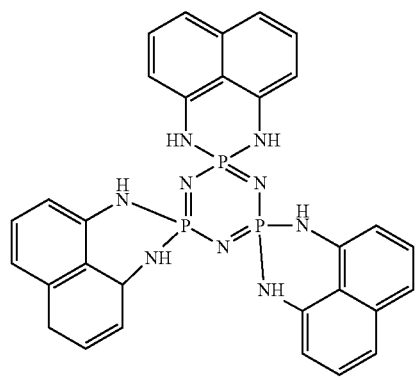

formula 32
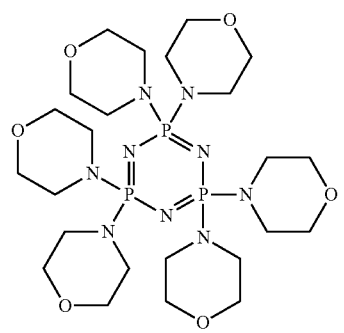

formula 33
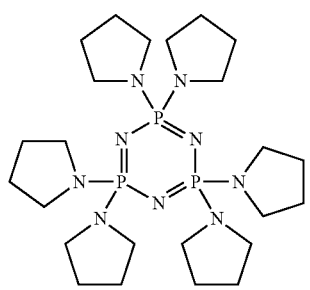

formula 34
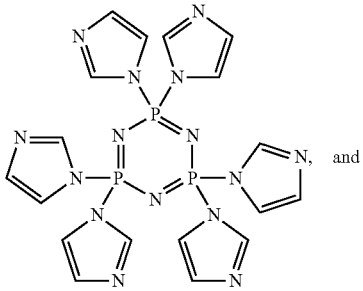

and formula 35
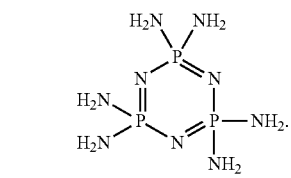

The cyclic compounds of the formulae 29-35 appear to be particularly suitable on the basis of their steric architecture and the electrical properties dictated by the substituent pattern, for the n-doping of electron transport layers. The molecular mass of these compounds, moreover, allows effective processing in vacuum processes.

Further in accordance with the invention is a method for producing n-conducting organic-electrical layers, wherein the organic n-dopant is deposited together with an organic electron transport material within a layer and the n-dopant and the electron transport material are reacted. Without being tied to a theory, it is believed that the reacting here may take place according to the reaction mechanism indicated above. There may therefore first be electrostatic interaction of the n-dopants of the invention with the electron transport materials, possibly leading subsequently to a transfer of electrons to the electron transport materials. This reaction may take place automatically, on the basis of suitable reaction kinetics, through the simultaneous deposition in a layer. Depending on the electron transport material selected and the n-dopant used, the reaction may also take place via subsequent thermal excitation. For this method it is possible to use the common electron transport materials which are familiar to the skilled person in the context of organic electronics. Both materials may be deposited from the wet phase and/or by means of a vacuum process. The aminophosphazene serves as an n-dopant here and may develop its doping effect either by coevaporation with an electron transport material or by mixing of an aminophosphazene with an ETM followed by liquid processing (e.g. spincoating, inkjet printing, slot coating etc.). On account of their ready solubility even in highly apolar solvents, the aminophosphazene bases are especially suitable for liquid processing. The larger molecules (e.g., a P4 base) are very stable thermally and can be vaporized in a high vacuum in the desired temperature range without decomposition, so making them suitable for vacuum processing.

In one particular embodiment of the inventive method, the organic electron transport material may be selected from the group consisting of 2,2',2"-(1,3,5-benzinetriyl)tris(1-phenyl-1-H-benzimidazole), 2-(4-biphenylyl)-5-(4-tert-butylphenyl)-1,3,4-oxadiazole; 2,9-dimethyl-4,7-diphenyl-1,10-phenanthroline (BCP), 8-hydroxyquinolinolatolithium; 4-(naphthalen-1-yl)-3,5-diphenyl-4H-1,2,4-triazole; 1,3-bis[2-(2,2'-bipyridine-6-yl)-1,3,4-oxadiazo-5-yl]benzene; 4,7- diphenyl-1,10-phenanthroline (BPhen); 3-(4-biphenylyl)-4-phenyl-5-tert-butylphenyl-1,2,4-triazole; bis(2-methyl-8-quinolinolate)-4-(phenylphenolato)aluminum; 6,6'-bis[5-(biphenyl-4-yl)-1,3,4-oxadiazo-2-yl]-2,2'-bipyridyl; 2-phenyl-9,10-di(naphthalen-2-yl)anthracene; 2,7-bis[2-(2,2'-bipyridine-6-yl)-1,3,4-oxadiazo-5-yl]-9,9-dimethylfluorene; 1,3-bis[2-(4-tert-butylphenyl)-1,3,4-oxadiazo-5-yl]benzene; 2-(naphthalen-2-yl)-4,7-diphenyl-1,10-phenanthroline; 2,9-bis(naphthalen-2-yl)-4,7-diphenyl-1,10-phenanthroline; tris(2,4,6-trimethyl-3-(pyridin-3-yl)phenyl)borane; 1-methyl-2-(4-(naphthalen-2-yl)phenyl)-1H-imidazo[4,5-f][1,10]phenanthroline; phenyldipyrenylphosphine oxide; 3,3',5,5'-tetra[(m-pyridyl)phen-3-yl]biphenyl; 1,3,5-tris[(3-pyridyl)phen-3-yl]benzene; 4,4'-bis(4,6-diphenyl-1,3,5-triazin-2-yl)biphenyl; 1,3-bis[3,5-di(pyridin-3-yl)phenyl]benzene; diphenylbis(4-(pyridin-3-yl)phenyl)silane; 3,5-di(pyren-1-yl)pyridine; 1,3,5-tri(p-pyrid-3-ylphenyl)benzene; 2,4,6-tris(3'-(pyridin-3-yl)biphenyl-3-yl)-1,3,5-triazine; naphthalenetetracarboxylic dianhydride and its imides; perylenetetracarboxylic dianhydride and its imides; and materials based on siloles having a silacyclopentadiene unit. These electron transport materials may be reacted readily with the aminophosphazene dopants of the invention, on account of their electronic properties (HOMO/LUMO level). The additional incorporation of the aminophosphazene dopants can be used in particular to significantly increase the conductivity of the electron transport materials.

Further in accordance with the invention is an n-conducting organic-electrical layer which has been produced by a method of the invention. By means of a method presented above, it is possible to obtain homogeneous layers which are suitable for use in components of organic electronics. As already mentioned, the aminophosphazenes of the invention are particularly suitable to be processed by the standard methods of organic electronics. Moreover, a feature of the layers produced in this way is that they exhibit low crystallization tendency, so contributing to a longer life of organic components containing these layers. The increased conductivity of the electron transport layers, moreover, results in greater efficiency of the layers.

Also in accordance with the invention is an organic-electrical component, wherein the component comprises an n-conducting organic-electrical layer of the invention. The n-dopants of the invention and the methods of the invention for producing doped electron transport layers can be utilized to particularly good effect for the production of organic-electrical components. This way, long-lived, efficient components are obtained. The organic-electrical components in this context may comprise the standard components of organic electronics, namely organic photodiodes, solar cells, bipolar and field-effect transistors, and organic light-emitting diodes.

For further advantages and features of the above-described method, reference is hereby made explicitly to the explanations in connection with the organic n-dopant of the invention, the layers of the invention, and the components of the invention. Inventive features and advantages of the n-dopants of the invention are also intended to be applicable and disclosed for the layers of the invention, the method of the invention, and the organic components of the invention, and vice versa. The invention also embraces all combinations of at least two features disclosed in the description and/or in the claims.

The above-described properties, features, and advantages of this invention, and also the manner in which they are achieved, will become clearer and more readily understandable in connection with the following description of the exemplary embodiments, which are elucidated in more detail in association with the drawings.

EXAMPLES

The suitability of the n-dopants in accordance with the invention is demonstrated using the doping of various organic electron conductors. The n-dopant used is the aminophosphazene base $P_4$-$^t$Bu

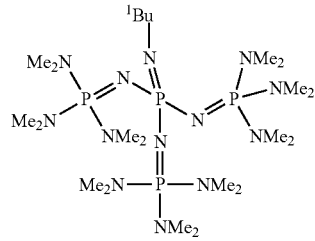

I. Purification of the n-dopant

The phosphazene base $P_4$-$^t$Bu is available commercially from Sigma-Aldrich as a 0.8 M solution in n-hexane. The solution (1 ml) was introduced into a Schlenk tube in a glovebox and evaporated to dryness by reduced pressure. The white residue was subsequently sublimed three times at 105° C. under a high vacuum ($3-4 \times 10^{-6}$ mbar). The product was obtained in a yield of 73% as a white, partially crystalline solid.

II. Doping of Various Electron-conducting Matrix Materials with an n-dopant of the Invention As a reference for the doped layer, a majority charge transfer component was produced in each case, with the following component architecture:

glass substrate
ITO (indium-tin oxide) as anode
200 nm electron-conducting matrix material
calcium as cathode
aluminum as outer layer to protect the reactive Ca cathode Components each with 15 pixels and a pixel area of 4 mm$^2$ were produced.

These reference elements are compared in each case with elements in which the layer of electron-conducting matrix material has been doped additionally with an n-dopant of the invention ($P_4$-$^t$Bu).

In each case 4 different electron-conducting matrix materials were used:
1. ETM-036, Merck
2. ETM-019, Merck
3. TMM-004, Merck
4. Alq3

The layer thickness fraction (volume %) of dopant is 18% in cases 1. to 3., whereas 17% of dopant was used in the doping of Alq3.

III. Current-voltage Characteristic Curves of the Various Electron Transport Layers The comparison of the doped electron-conducting matrix materials with the undoped matrix materials is shown in FIGS. 4-7.

Figure 4:
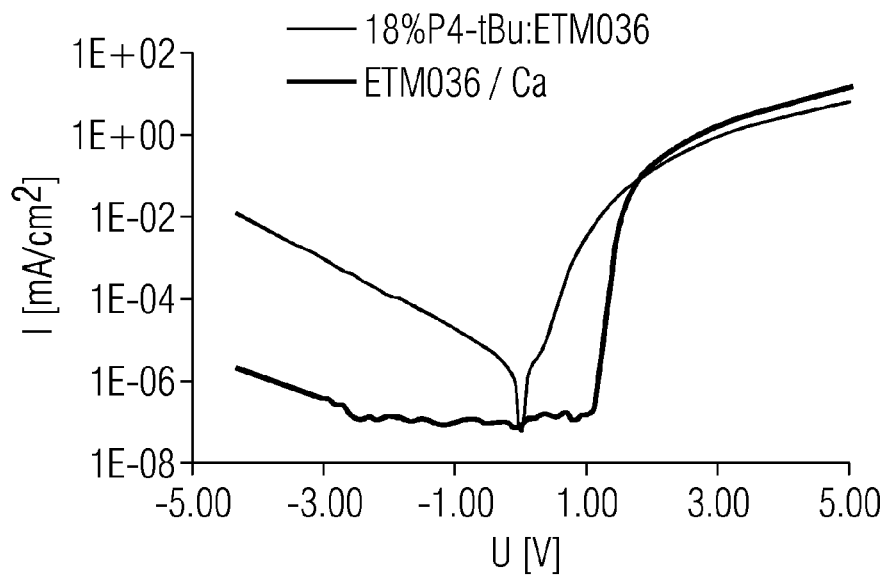
FIG. 4 shows an IV characteristic curve of an electron-conducting matrix material (ETM036, Merck) which has been doped with an n-dopant of the invention (P4-tBu). The characteristic lines are discussed in the examples.
Figure 5:
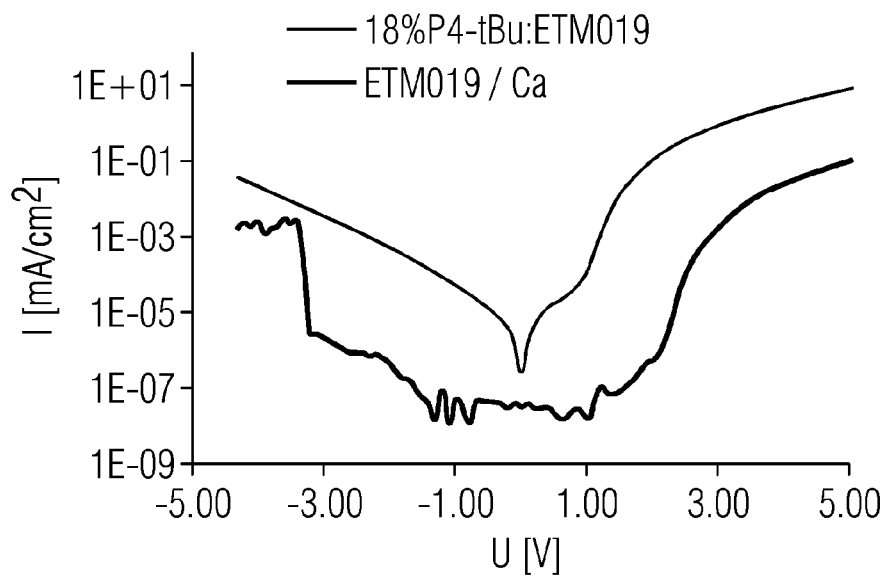
FIG. 5 shows an IV characteristic curve of a further electron-conducting matrix material (ETM019, Merck) which has been doped with an n-dopant of the invention (P4-tBu). The characteristic lines are discussed in the examples.
Figure 6:
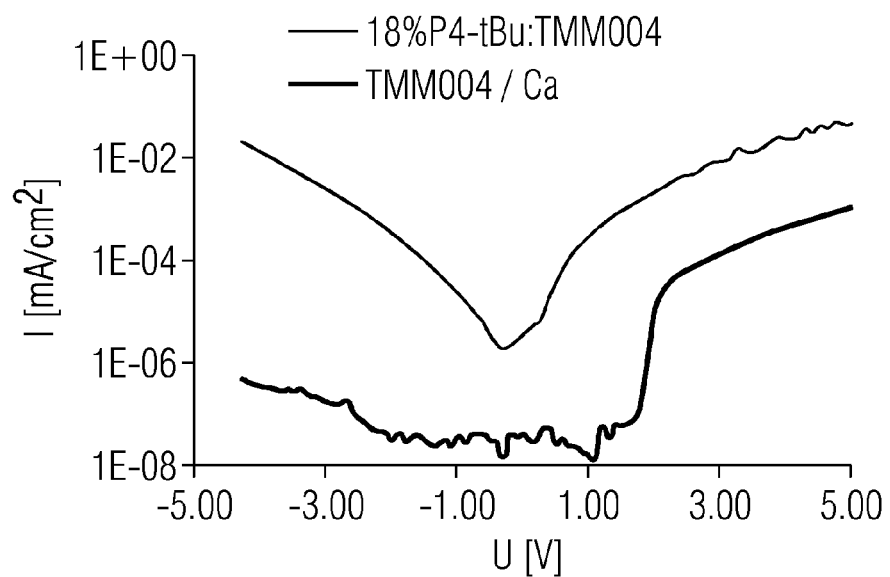
FIG. 6 shows an IV characteristic curve of a further electron-conducting matrix material (TMM004, Merck) which has been doped with an n-dopant of the invention (P4-tBu). The characteristic lines are discussed in the examples.
Figure 7:
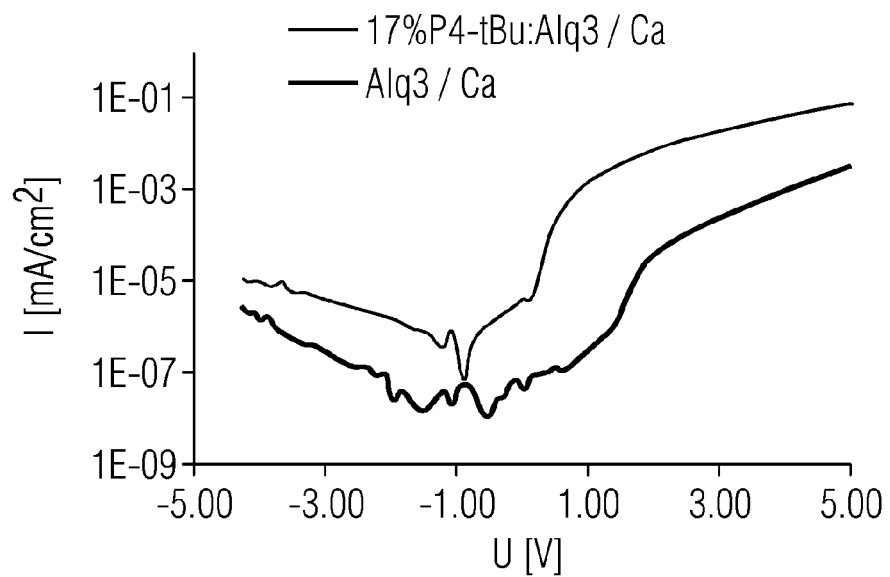
FIG. 7 shows an IV characteristic curve of a further electron-conducting matrix material (Alq3, aluminum tris (8-hydroxyquinoline)) which has been doped with an n-dopant of the invention (P4-tBu). The characteristic lines are discussed in the examples.

FIG. 4 shows the current-voltage characteristic curve for the doping of ETM-036, FIG. 5 for the doping of ETM-019, FIG. 6 for the doping of TMM-004, and FIG. 7 for the doping of Alq3, in each case with $P_4$-$^t$Bu.

For all of the components it can be shown that the current density in the doped layer rises sharply above and below 0 V, whereas for the intrinsic (undoped) layer (black curve) a typical diode characteristic curve is observed. In the case of the undoped layers, a significant overvoltage (built-in voltage) is necessary before the current density rises. Moreover, in the case of the intrinsic layer, this occurs only at positive voltages, whereas the doped layers display increased current densities even at negative voltages. This also enables efficient electron injection on the part of the anode (ITO).

Accordingly, all electron-conducting matrix materials exhibit an improvement in the current-voltage behavior by virtue of the inventive doping.

Although the invention has been described and illustrated in greater detail by the preferred exemplary embodiment, the invention is not restricted by the examples disclosed, and other variations can be derived therefrom by the skilled person without leaving the scope of protection of the invention.

What is claimed is:

1. A method for producing an n-conducting organic-electrical layer, the method comprising:
depositing a n-dopant comprising at least one aminophosphazene group of the formula

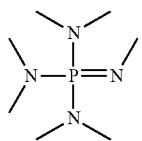

with an organic electron transport material, the organic electron transport material selected from the group consisting of 2,2',2"-(1,3,5-benzinetriyl)tris(1-phenyl-1-H-benzimidazole), 2-(4-biphenylyl)-5-(4-tert-butyl-phenyl)-1,3,4-oxadiazole; 2,9-dimethyl-4,7-diphenyl-1,10-phenanthroline (BCP), 8-hydroxyquinolinolatolithium; 4-(naphthalen-1-yl)-3,5-diphenyl-4H-1,2,4-triazole; 1,3-bis[2-(2,2'-bipyridine-6-yl)-1,3,4-oxadiazo-5-yl]benzene; 4,7-diphenyl-1,10-phenanthroline (Bphen); 3-(4-biphenylyl)-4-phenyl-5-tert-butylphenyl-1,2,4-triazole; bis(2-methyl-8-quinolinolate)-4-(phenylphenolato)aluminum; 6,6'-bis[5-(biphenyl-4-yl)-1,3,4-oxadiazo-2-yl]-2,2'-bipyridyl; 2-phenyl-9,10-di(naphthalen-2-yl)anthracene; 2,7-bis[2-(2,2'-bipyridine-6-yl)-1,3,4-oxadiazo-5-yl]-9,9-dimethylfluorene; 1,3-bis[2-(4-tert-butylphenyl)-1,3,4-oxadiazo-5-yl]benzene; 2-(naphthalen-2-yl)-4,7-diphenyl-1,10-phenanthroline; 2,9-bis(naphthalen-2-yl)-4,7-diphenyl-1,10-phenanthroline; tris(2,4,6-trimethyl-3-(pyridin-3-yl)phenyl)borane; 1-methyl -2-(4-(naphthalen-2-yl)phenyl)-1H-imidazo[4,5-f][1,10]phenanthroline; phenyldipyrenylphosphine oxide; 3,3',5,5'-tetra[(m-pyridyl)phen-3-yl]bi-phenyl; 1,3,5-tris[(3-pyridyl)phen-3-yl]benzene; 4,4'-bis(4,6-diphenyl-1,3,5-triazin-2-yl)bi-phenyl; 1,3-bis[3,5-di(pyridin-3-yl)phenyl]benzene; diphenylbis(4-(pyridin-3-)phenyl)silane; 3,5-di(pyren-1-yl)pyridine; 1,3,5-tri(p-pyrid-3-ylphenyl)benzene; 2,4,6-tris(3'-(pyridin-3-yl)biphenyl-3-yl)-1,3,5-triazine; perylenetetracarboxylic dianhydride and its imides; and materials based on siloles, having a silacyclopentadiene unit, and forming an n-conducting organic-electrical layer comprising from about 0.01% to about 30% by volume n-dopant.

2. A method according to claim 1, wherein the deposited n-dopant further comprises substituents $R^1$-$R^6$ according to the formula

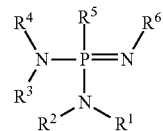

wherein $R^1$ to $R^4$ independently of one another are selected from the group consisting of C1-C60 saturated or unsaturated alkyls, cycloalkyls, heteroalkyls, and heterocycloalkyls, C1-C60 aryls, alkylaryls, and heteroaryls; $R^5$ is selected from $NR_2$ and $[-N=P(NR_2)_2-]_n$ where n=1 to 5; and $R^6$ comprises $[-P(NR_2)_2=N-]_n$ where n=1 to 5.

3. A method according to claim 1, wherein the deposited n-dopant has ≥2 to ≤7 aminophosphazene groups.

4. A method according to claim 1, wherein the deposited n-dopant comprises at least one compound of formulae 3-28:

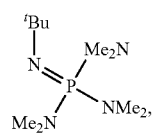

formula 3

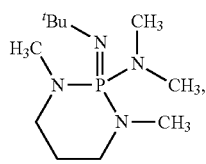

formula 4

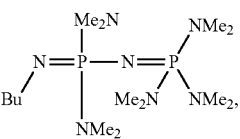

formula 5

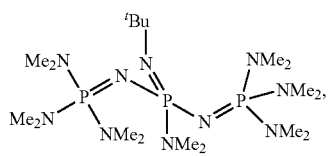

formula 6

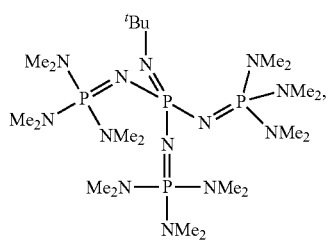

formula 7 formula 8
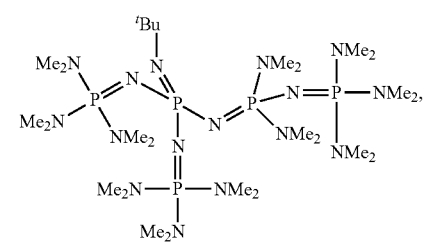
formula 9
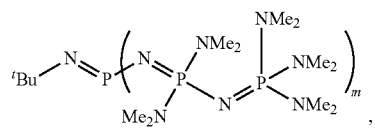
formula 10
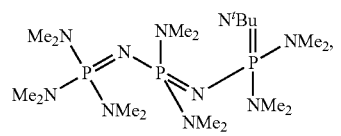
formula 11
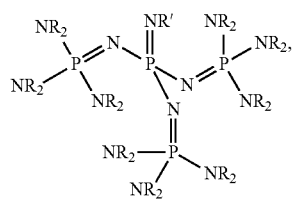
formula 12
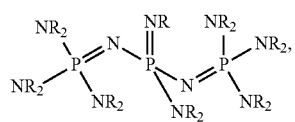
formula 13
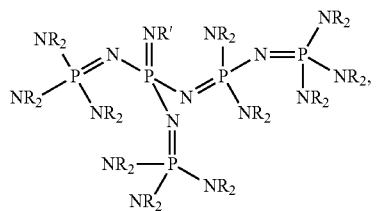
formula 14
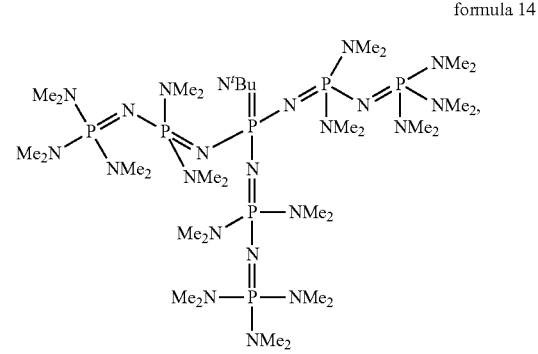
formula 15
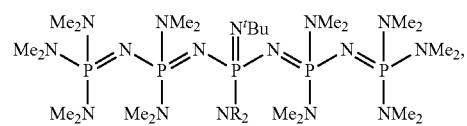
formula 16
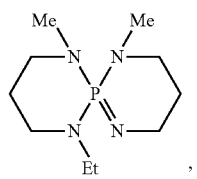
formula 17
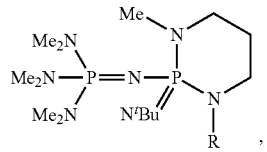
formula 18
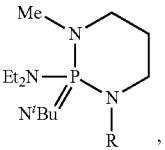
formula 19
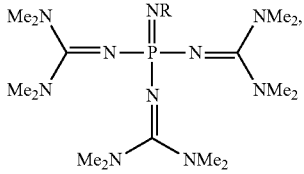
formula 20
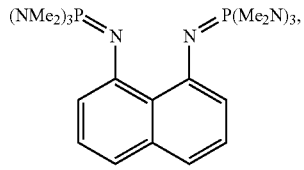
formula 21
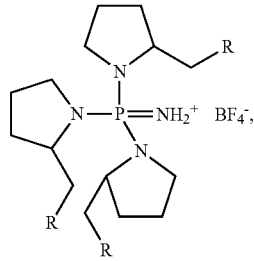
formula 22
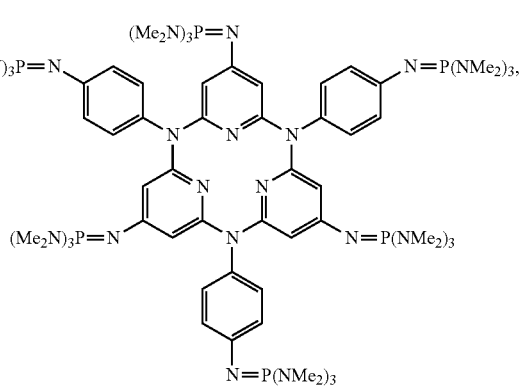

-continued

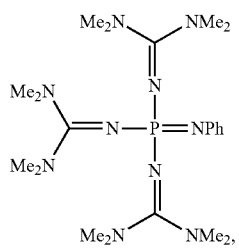
formula 23

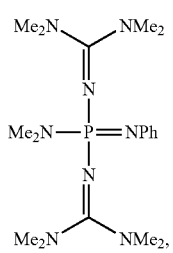
formula 24

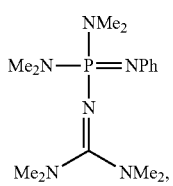
formula 25

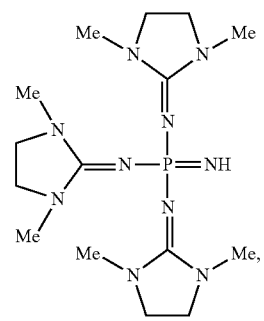
formula 26

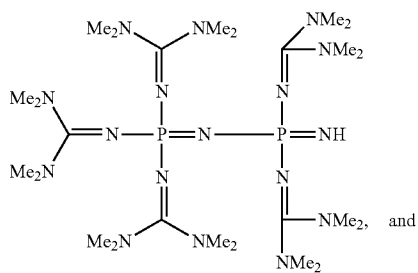
formula 27

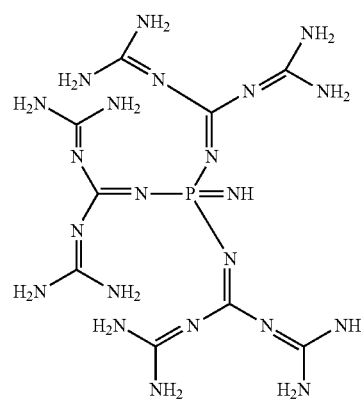
formula 28 where m in formula 9 is ≥1 and ≤5.

5. A method for producing n-conducting organic-electrical layers, the method comprising
depositing and reacting an n-dopant together with an organic electron transport material to form an n-conducting organic-electrical layer, wherein the n-dopant is characterized by the formula

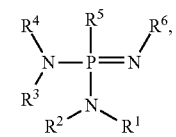

wherein substituents $R^1$ to $R^4$ independently of one another are selected from the group consisting of a bond, H, D, C1-C60 saturated or unsaturated alkyl, cycloalkyl, heteroalkyl, heterocycloalkyl; and C1-C60 aryl, alkylaryl, heteroaryl;

substituent $R^5$ is selected from $NR_2$ and $[-N=P(NR_2)_2-]_n$ wherein n=1 to 5;

substituent $R^6$ is selected from the group of R and $[-P(NR_2)_2=N-]_n$ where n=1 to 5, optionally the substituents independently of one another may be joined to form cyclic units; and the n-dopant is a compound having a noncyclic aminophosphazene scaffold, wherein the dopant comprises at least one compound of formulae 4-28:

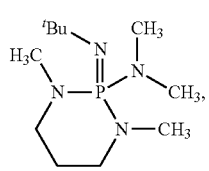
formula 4

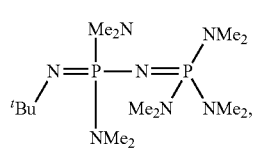
formula 5

-continued formula 6–21 (chemical structures)

-continued formula 22
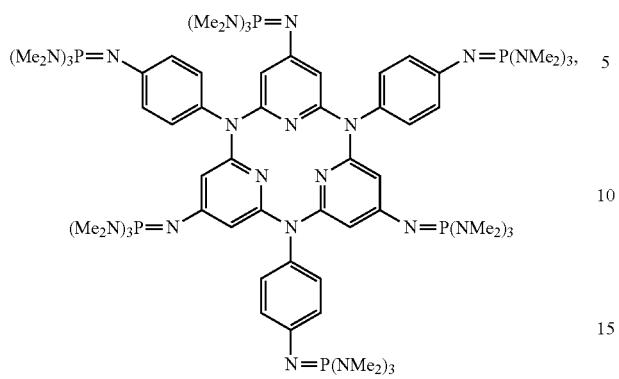

formula 23
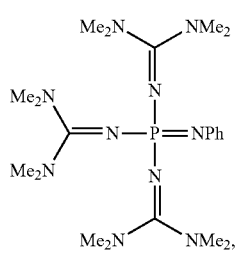

formula 24
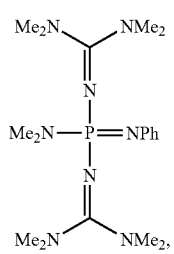

formula 25
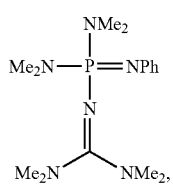

formula 26
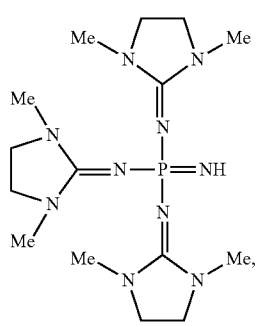

-continued formula 27
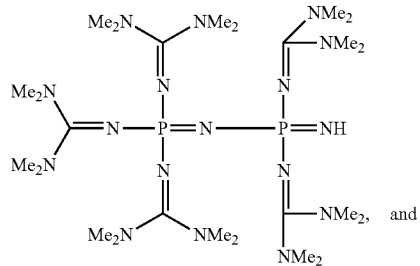

formula 28
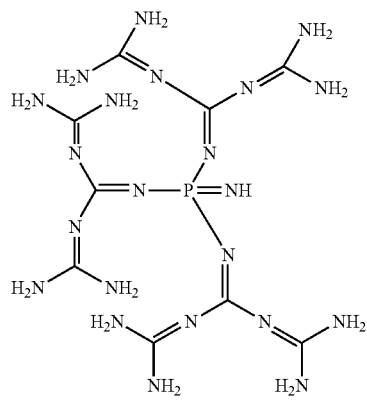

where m in formula 9 is ≥1 and ≤5.

6. A method for producing n-conducting organic-electrical layers, the method comprising
depositing and reacting an n-dopant together with an organic electron transport material to form an n-conducting organic-electrical layer, wherein the n-dopant is characterized by the formula

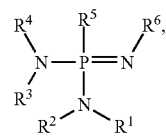

wherein substituents $R^1$ to $R^4$ independently of one another are selected from the group consisting of a bond, H, D, C1-C60 saturated or unsaturated alkyl, cycloalkyl, heteroalkyl, heterocycloalkyl; and C1-C60 aryl, alkylaryl, heteroaryl;
substituent $R^5$ is selected from $NR_2$ and $[-N=P(NR_2)_2-]_n$ wherein n=1 to 5;
substituent $R^6$ is selected from the group of R and $[-P(NR_2)_2=N-]_n$ where n=1 to 5, optionally the substituents independently of one another may be joined to form cyclic units; and
the n-dopant is a compound having a noncyclic aminophosphazene scaffold, wherein the organic electron transport material is selected from the group consisting of 2,2',2"-(1,3,5-benzinetriyl)tris(1-phenyl-1-H-benzimidazole), 2-(4-biphenylyl)-5-(4-tert-butylphenyl)-1,3,4-oxadiazole; 2,9-dimethyl-4,7-diphenyl-1,10-phenanthroline (BCP), 8-hydroxyquinolinolatolithium; 4-(naphthalen-1-yl)-3,5-diphenyl-4H-1,2,4-triazole; 1,3-bis[2-(2,2'-bipyridine-6-yl)-1,3,4-oxadiazo-5-yl]benzene; 4,7-diphenyl-1,10-phenanthroline (BPhen); 3-(4- biphenylyl)-4-phenyl-5-tert-butylphenyl-1,2,4-triazole; bis(2-methyl-8-quinolinolate)-4-(phenylphenolato)aluminum; 6,6'-bis[5-(biphenyl-4-yl)-1,3,4-oxadiazo-2-yl]-2,2'-bipyridyl; 2-phenyl-9,10-di(naphthalen-2-yl)anthracene; 2,7-bis[2-(2,2'-bipyridine-6-yl)-1,3,4-oxadiazo-5-yl]-9,9-dimethylfluorene; 1,3-bis[2-(4-tert-butylphenyl)-1,3,4-oxadiazo-5-yl]benzene; 2-(naphthalen-2-yl)-4,7-diphenyl-1,10-phenanthroline; 2,9-bis(naphthalen-2-yl)-4,7-diphenyl-1,10-phenanthroline; tris(2,4,6-trimethyl-3-(pyridin-3-yl)phenyl)borane; 1-methyl-2-(4-(naphthalen-2-yl)phenyl)-1H-imidazo[4,5-f][1,10]phenanthroline; phenyldipyrenylphosphine oxide; 3,3',5,5'-tetra[(m-pyridyl)phen-3-yl]biphenyl; 1,3,5-tris[(3-pyridyl)phen-3-yl]benzene; 4,4'-bis(4,6-diphenyl-1,3,5-triazin-2-yl)biphenyl; 1,3-bis[3,5-di(pyridin-3-yl)phenyl]benzene; diphenylbis(4-(pyridin-3-yl)phenyl)silane; 3,5-di(pyren-1-yl)pyridine; 1,3,5-tri(p-pyrid-3-ylphenyl)benzene; 2,4,6-tris(3'-(pyridin-3-yl)biphenyl-3-yl)-1,3,5-triazine; perylenetetracarboxylic dianhydride and its imides; and materials based on siloles, having a silacyclopentadiene unit.

7. A method for producing an n-conducting organic-electrical layer, the method comprising:

depositing a n-dopant comprising ≥2 and ≤7 aminophosphazene groups of the formula

together with an organic electron transport material to form an n-conducting organic-electrical layer comprising from about 0.01% to about 30% by volume n-dopant volume, wherein the organic electron transport material is selected from the group consisting of 2,2',2''-(1,3,5-benzinetriyl)tris(1-phenyl-1-H-benzimidazole), 2-(4-biphenylyl)-5-(4-tert-butylphenyl)-1,3,4-oxadiazole; 2,9-dimethyl-4,7-diphenyl-1,10-phenanthroline (BCP), 8-hydroxyquinolinolatolithium; 4-(naphthalen-1-yl)-3,5-diphenyl-4H-1,2,4-triazole; 1,3-bis[2-(2,2'-bipyridine-6-yl)-1,3,4-oxadiazo-5-yl]benzene; 4,7-diphenyl-1,10-phenanthroline (BPhen); 3-(4-biphenylyl)-4-phenyl-5-tert-butylphenyl-1,2,4-triazole; bis(2-methyl-8-quinolinolate)-4-(phenylphenolato)aluminum; 6,6'-bis[5-(biphenyl-4-yl)-1,3,4-oxadiazo-2-yl]-2,2'-bipyridyl; 2-phenyl-9,10-di(naphthalen-2-yl)anthracene; 2,7-bis[2-(2,2'-bipyridine-6-yl)-1,3,4-oxadiazo-5-yl]-9,9-dimethylfluorene; 1,3-bis[2-(4-tert-butylphenyl)-1,3,4-oxadiazo-5-yl]benzene; 2-(naphthalen-2-yl)-4,7-diphenyl-1,10-phenanthroline; 2,9-bis(naphthalen-2-yl)-4,7-diphenyl-1,10-phenanthroline; tris(2,4,6-trimethyl-3-(pyridin-3-yl)phenyl)borane; 1-methyl-2-(4-(naphthalen-2-yl)phenyl)-1H-imidazo[4,5-f][1,10]phenanthroline; phenyldipyrenylphosphine oxide; 3,3',5,5'-tetra[(m-pyridyl)phen-3-yl]bi-phenyl; 1,3,5-tris[(3-pyridyl)phen-3-yl]benzene; 4,4'-bis(4,6-diphenyl-1,3,5-triazin-2-yl)bi-phenyl; 1,3-bis[3,5-di(pyridin-3-yl)phenyl]benzene; diphenylbis(4-(pyridin-3-yl)phenyl)silane; 3,5-di(pyren-1-yl)pyridine; 1,3,5-tri(p-pyrid-3-ylphenyl)benzene; 2,4,6-tris(3'-(pyridin-3-yl)bi-phenyl-3-yl)-1,3,5-triazine; perylenetetracarboxylic dianhydride and its imides; and materials based on siloles, having a silacyclopentadiene unit.

8. A method for producing an n-conducting organic-electrical layer, the method comprising:

depositing a n-dopant comprising ≥2 and ≤7 aminophosphazene groups of the formula

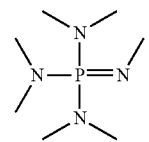

together with an organic electron transport material to form an n-conducting organic-electrical layer comprising from about 0.01 to about 30% by volume n-dopant volume, wherein the n-dopant comprises at least one of the following formulae 31-35 below:

formula 31

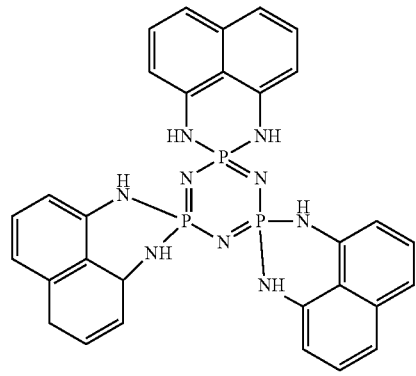

formula 32

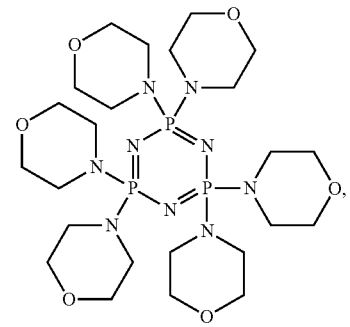

formula 33

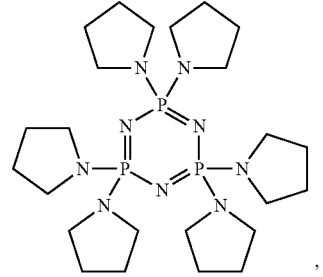

-continued

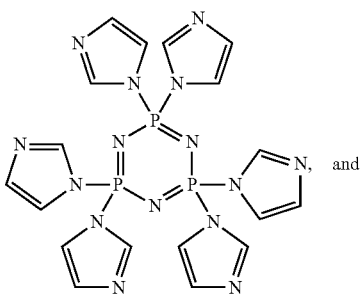
formula 34

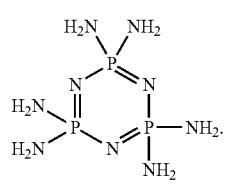
formula 35

9. A method for producing an n-conducting organic-electrical layer, the method comprising:
 depositing a n-dopant comprising ≥2 and ≤7 aminophosphazene groups of the formula

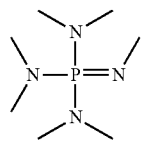

together with an organic electron transport material to form an n-conducting organic-electrical layer comprising from about 0.01% to about 30% by volume n-dopant, wherein the n-dopant comprises at least one compound of formulae 4-28:

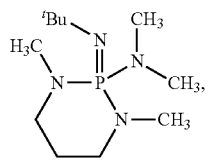
formula 4

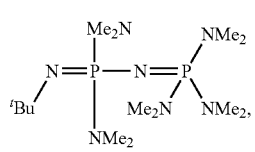
formula 5

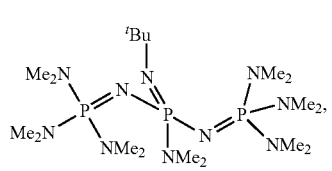
formula 6

-continued

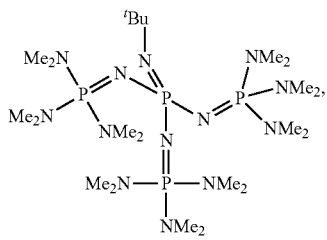
formula 7

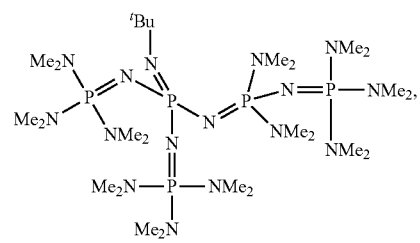
formula 8

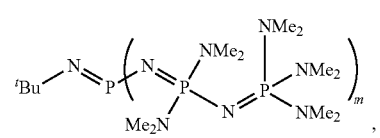
formula 9

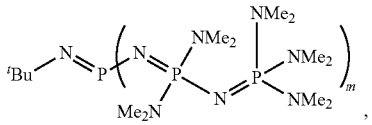
formula 10

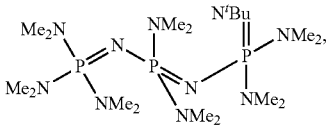
formula 11

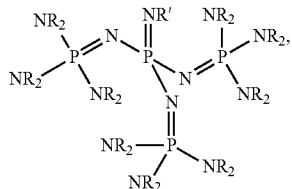
formula 12

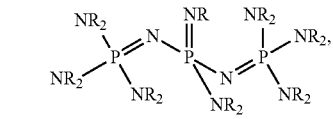
formula 13

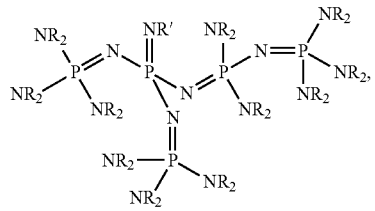

-continued
formula 14
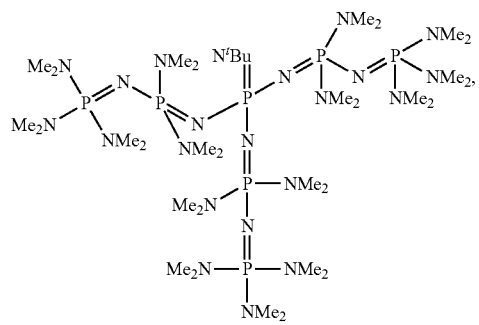
formula 15
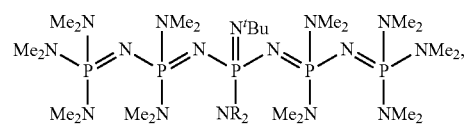
formula 16
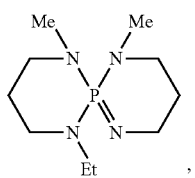
formula 17
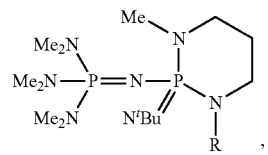
formula 18
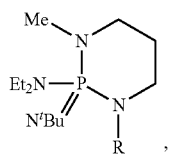
formula 19
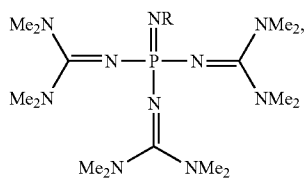
formula 20
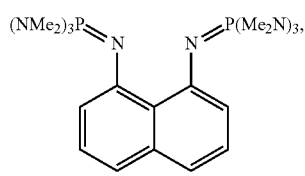
formula 21
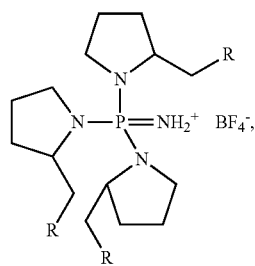
-continued
formula 22
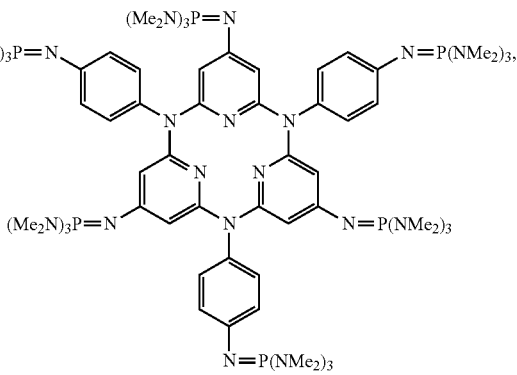
formula 23
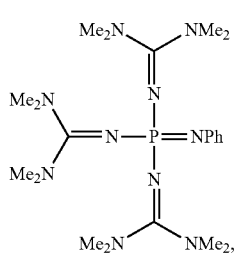
formula 24
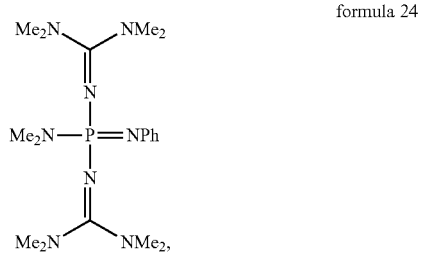
formula 25
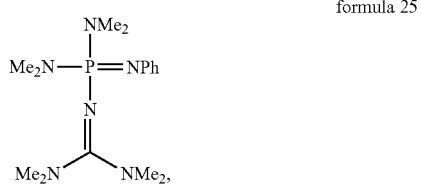
formula 26
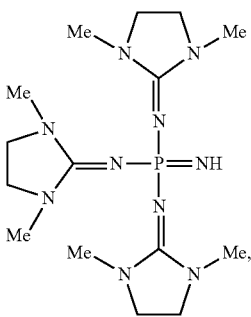

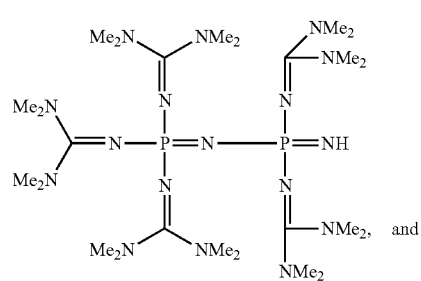
formula 27
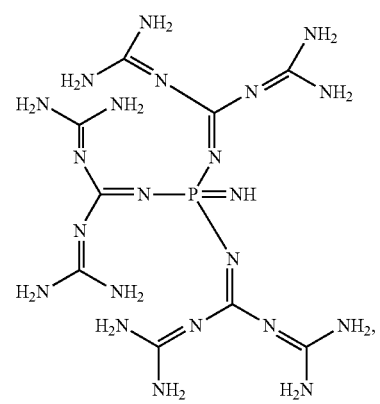
formula 28
where m in formula 9 is ≥1 and ≤5.
* * * * *